United States Patent [19]

Ludwigs

[11] Patent Number: 4,886,453
[45] Date of Patent: Dec. 12, 1989

[54] BUILDING KIT FOR AN APPARATUS FOR MANUFACTURING TOTAL PROSTHEISES FOR UPPER AND LOWER JAWS

[76] Inventor: Horst Ludwigs, Lenbachstrasse 33, D-4800 Bielefeld 1, Fed. Rep. of Germany

[21] Appl. No.: 130,385

[22] PCT Filed: Feb. 27, 1987

[86] PCT No.: PCT/EP87/00119
    § 371 Date: Oct. 26, 1987
    § 102(e) Date: Oct. 26, 1987

[87] PCT Pub. No.: WO87/05202
    PCT Pub. Date: Sep. 11, 1987

[30] Foreign Application Priority Data

Jun. 27, 1986 [DE] Fed. Rep. of Germany ... 8617182[U]
Sep. 23, 1986 [DE] Fed. Rep. of Germany ... 8625405[U]
Feb. 27, 1987 [DE] Fed. Rep. of Germany ... 8605333[U]

[51] Int. Cl.⁴ ............................................. A61C 11/00
[52] U.S. Cl. ..................................................... 433/54
[58] Field of Search ....................... 433/54, 55, 61, 62, 433/63, 64, 65

[56] References Cited

U.S. PATENT DOCUMENTS 2,270,561  1/1942  Sanborn ................................ 433/63

FOREIGN PATENT DOCUMENTS 206667  8/1980  United Kingdom ................... 433/65

Primary Examiner—Robert Peshock
Attorney, Agent, or Firm—William A. Drucker

[57] ABSTRACT

The module for an apparatus (system) to produce upper and lower jaw full prostheses has an instrument holder (66) consisting of a baseplate (3), supporting two upright pillars (4) and a tilting arm (6) that can be pivoted on a horizontal axis (5) around the pillars (4), on which auxiliary instruments developed for individual work processes can be adapted.

In terms of auxiliary instruments, the module has an infinitely adjustable levelling table (9) set on the baseplate (3), a lower jaw alignment key (10), an impression or mounting plate (7, 8), an upper jaw model alignment key, a domed setting aid for correct setting of teeth on the lower jaw full prosthesis and a domed setting aid with dummy tooth for correct setting of the 1st right and left tooth on lower jaw full prostheses, which can be attached to the instrument holder (66) in a secure position and interchanged.

19 Claims, 11 Drawing Sheets

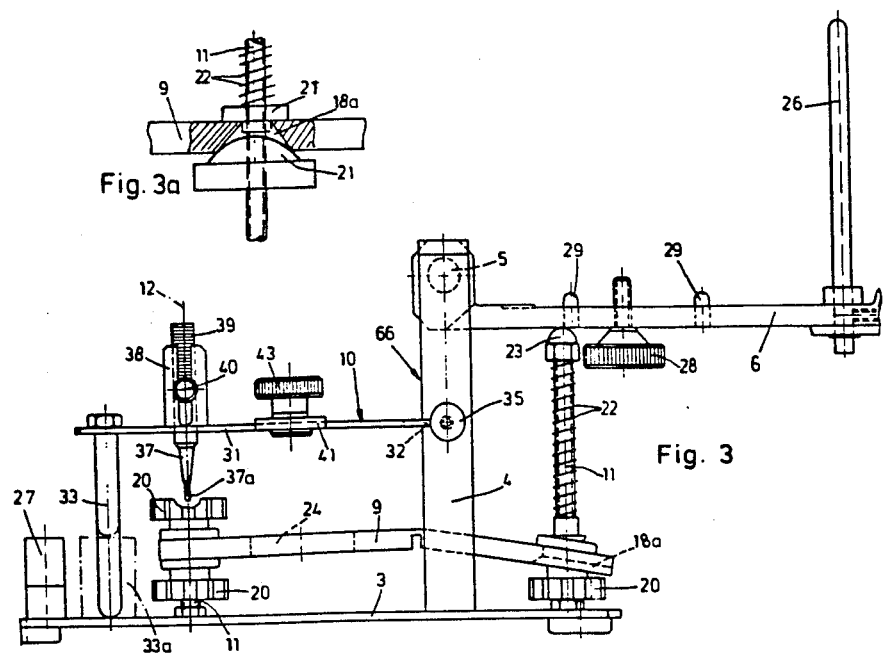
Fig. 3a
Fig. 3
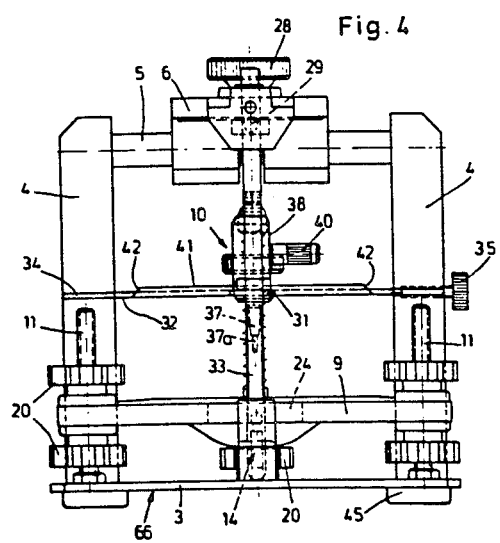
Fig. 4

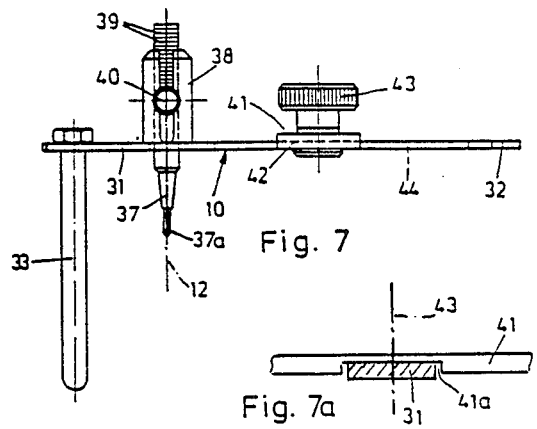
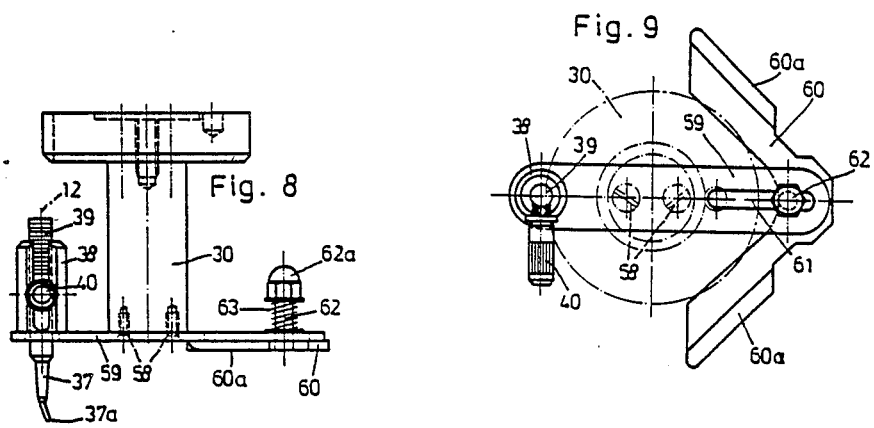
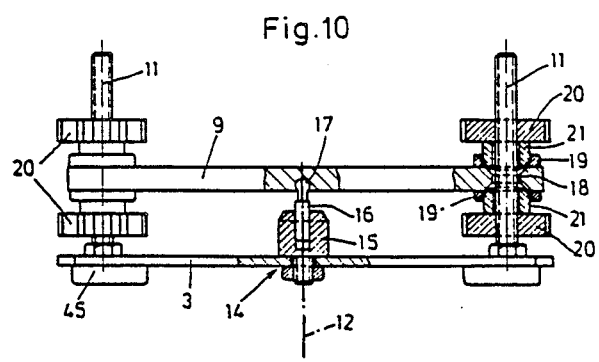

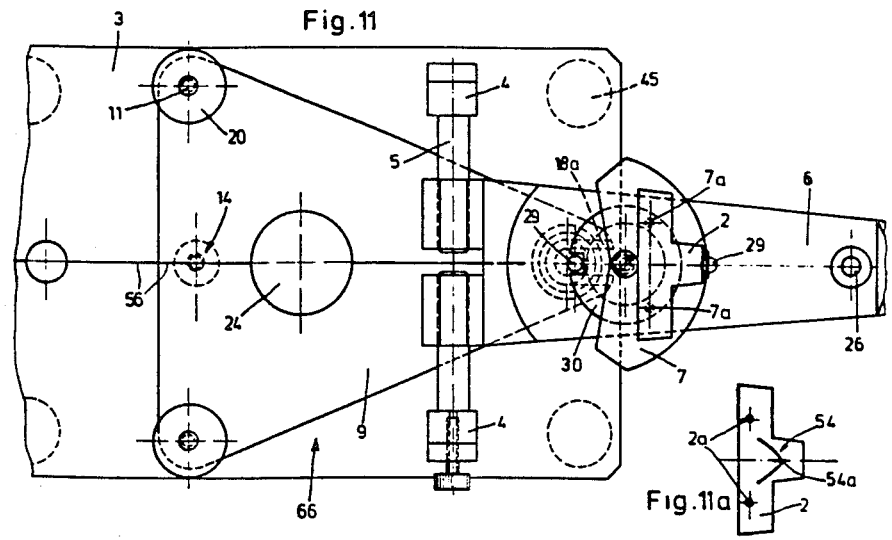
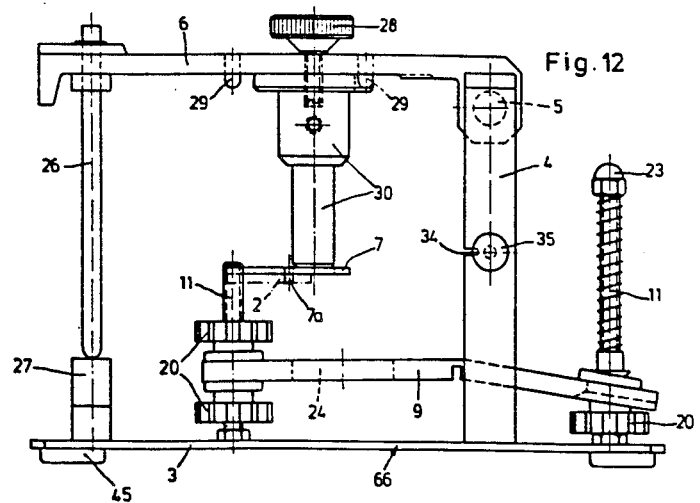

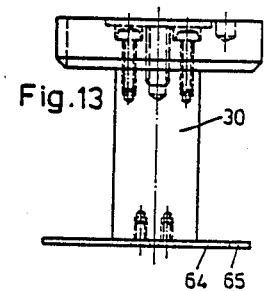
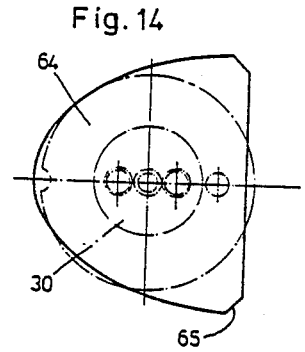
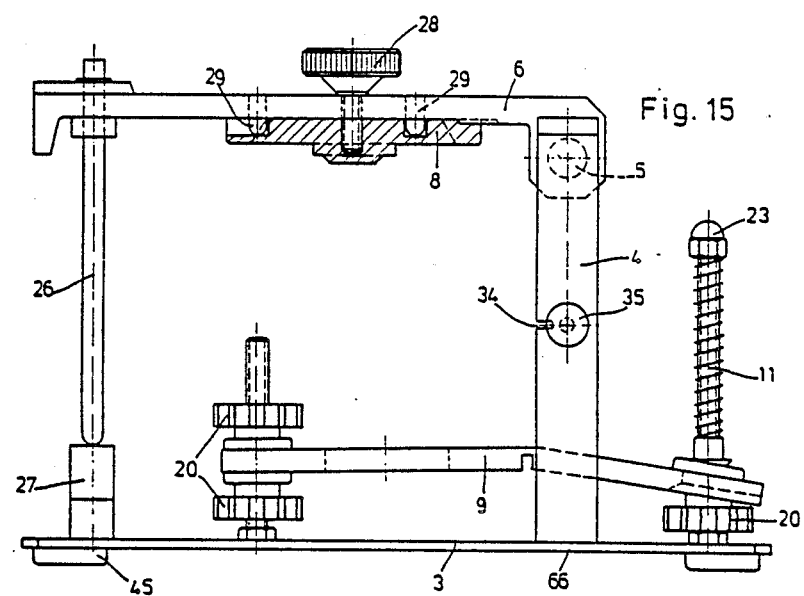

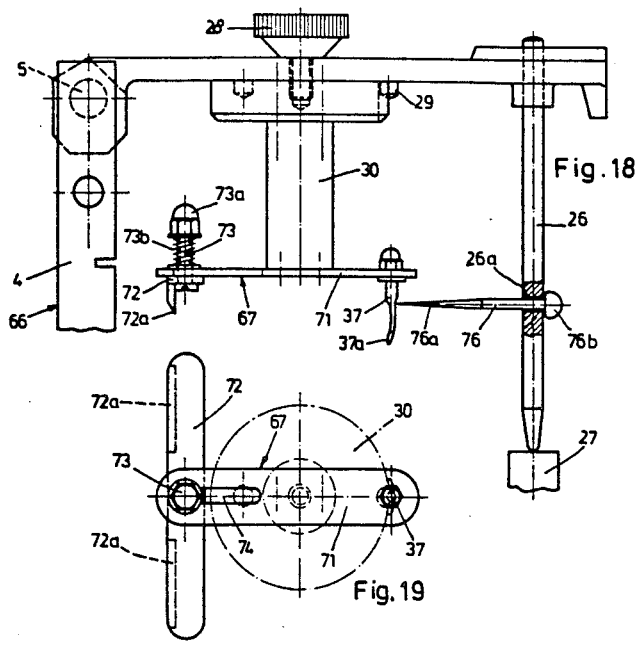
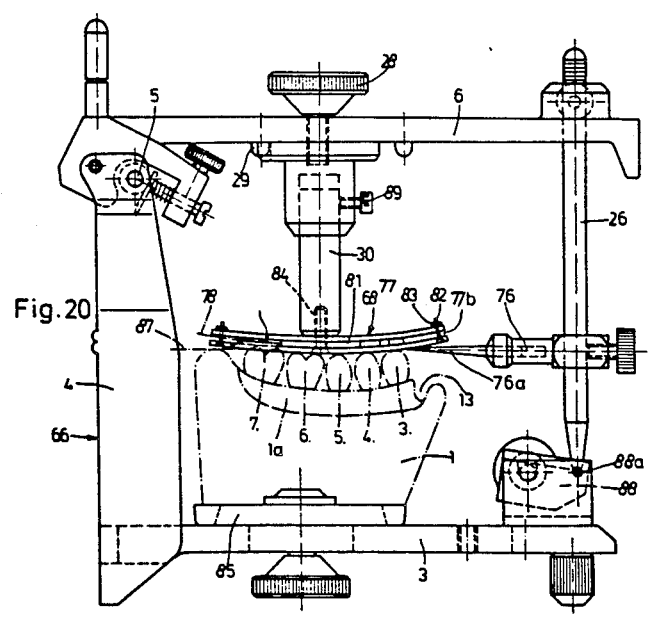

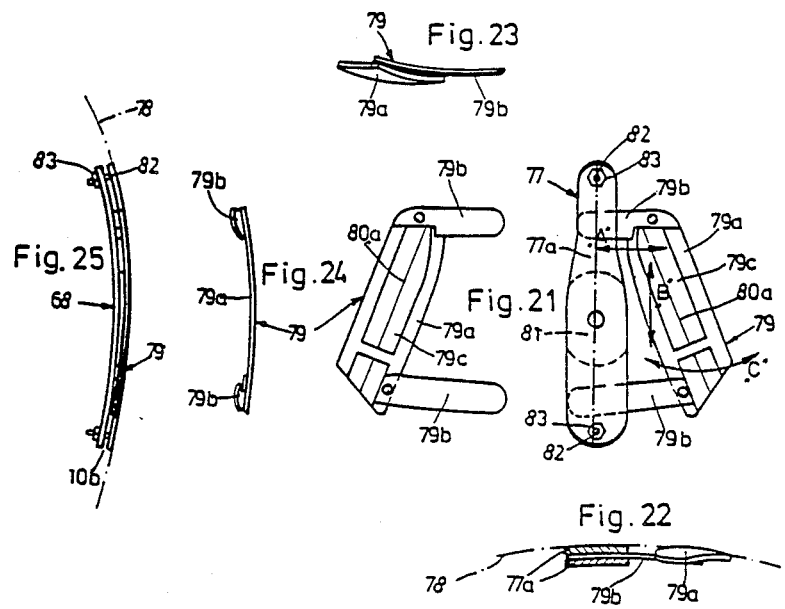
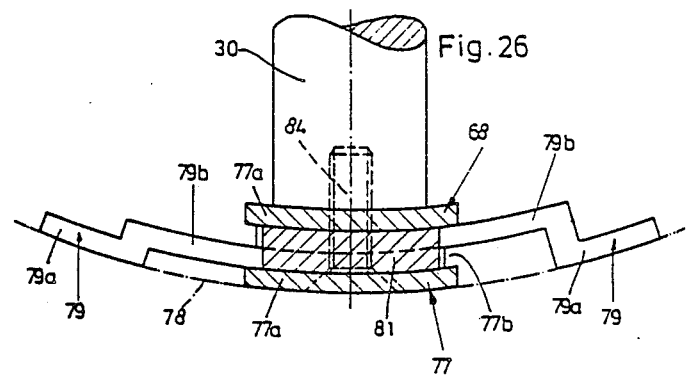
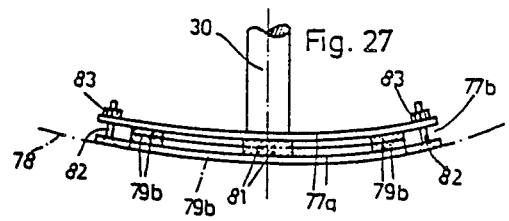

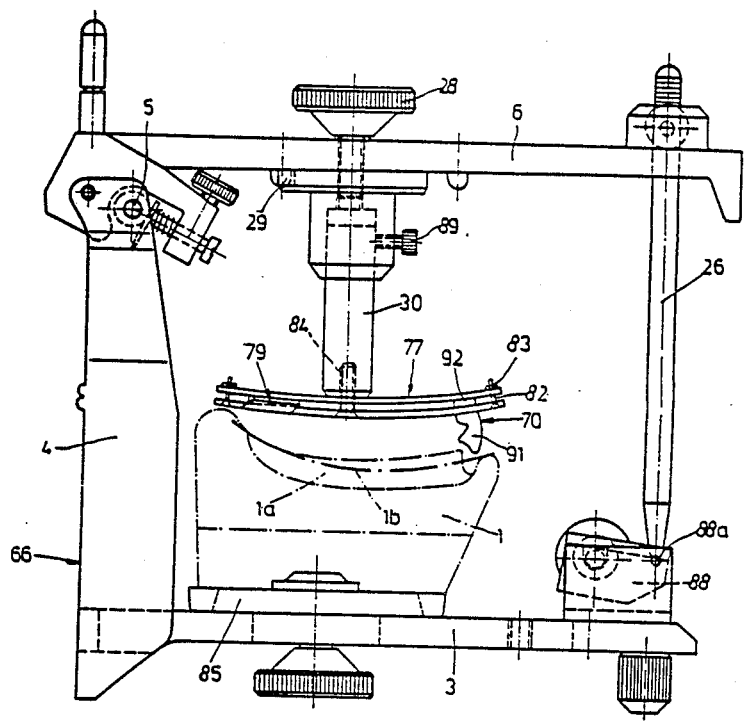
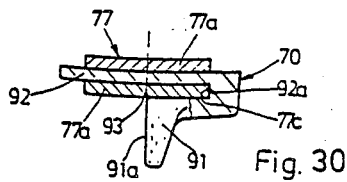
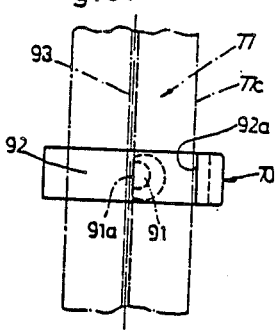

BUILDING KIT FOR AN APPARATUS FOR MANUFACTURING TOTAL PROSTHEISES FOR UPPER AND LOWER JAWS

The invention concerns the construction of a module of simple design, that is easy to handle, to form an apparatus with alignment, adjustment, measuring and display instruments for individual full prostheses with optimum accuracy in execution of the individual work processes.

This task is resolved with the invention by the characteristic features described in patent claim 1.

In addition, the purpose of the invention is to permit correct fixing of the lower jaw model for adjustment in articulators with this module, so that production of correctly positioned average bite templates related to mastication is possible at the same time with integrated centric scribing plates for drawing the "Gothic arch" for stylus registration.

A further task of the invention is to create a setting aid that is simply assembled and easy to handle, with which teeth can be set correctly aligned in lower jaw full prostheses, easily and securely. In addition, a setting aid for correctly aligned assembly of the right and left front teeth should be achieved with lower jaw full prostheses.

In addition, the purpose of the invention is to obtain an alignment aid with the module, to be used for adjustment of upper jaw models which are asymmetrical and vary in size, and can be used as reference points for the hard palate as well as the covering fold in the area of the labial frenulum.

In addition, the module shall comprise a impression plate as a bite template for the upper and/or lower jaw with or without stylus for a centric scribing plate, which shall be constructed separately for each jaw or usable for both jaws.

These tasks are resolved in the characteristic features of the subsidiary claims, which represent advantageous further forms of the features of patent claim 1.

The subject of the invention does not only extend to the features of the individual claims, but also to combinations of these.

The module as per the invention includes an instrument holder and interchangeable auxiliary instruments mounted on or in it, working in conjunction with each other and with the instrument holder, so that accurate adjustment is possible with easy handling for the individual work processes to be carried out with optimum accuracy in execution.

The instrument holder, which can be combined as an adjustment and levelling device, ensures sound fixing of the lower jaw models in an easy secure manner for production of bite templates or subsequent adjustment in the articulators to be used for setting.

By means of a levelling table that can be adjusted in height and inclination in any direction, and an alignment key which is adaptable in the instrument holder, by the possibility of adjusting the lower jaw model on the levelling table in the horizontal plane and by fixing with magnetic force, it is possible to determine the three salient alignment points in geometric terms of the articulator to be used. In addition, a bite wall template which can be fixed to the apparatus will permit exact alignment of the bite wall height and integration of a centric scribing plate for stylus registration.

Similarly the upper jaw model can be adjusted, but using the two hard palate sections and covering fold in the labium frenulum area as reference points. Moreover, with the upper jaw model, the bite wall height can be defined according to the mastication plane in conjunction with a bite wall template that can be fixed to the instrument holder.

With this apparatus, the geometrically correct position of the upper and lower jaw model can be determined individually for each patient within the articulator geometry, so that optimum seating of the prostheses can be achieved.

By means of the dome-shaped setting aid, teeth can be set at an inclination corresponding to the compensation curve formed by the dome, which can be defined exactly in relation to the values of the lower jaw model determined exactly using the adjusted inserts. By simple, optional adjustment of the insert or inserts, exact alignment on the central fissure line is possible. Positionally correct setting of the teeth, in relation to the jaw ridge, can be checked with the transparent inserts.

In addition, by means of the setting aid, the right or left lower front tooth (1st tooth) can be set in the correct position in a wax base which forms a flat covering on the jaw ridge, following its shape, within the obtained limits of the impression. This setting aid can be easily and accurately adjusted on a centreline and in a sagittal plane on a mount for the 1st left or right tooth, so that this can be set in the correct position, following the same procedure for correct positioning of the 2nd and 3rd teeth.

Setting in the correct position in this way facilitates alignment of inserts with marking lines on the central fissure line for setting the remaining lower teeth. In addition, the alignment bar permits exact adjustment to the hard palate, even with upper jaw models which differ in size and are asymmetrical.

By means of the drawings, construction examples as per the invention are explained in more detail below:

FIG. 1 shows a perspective view of the instrument holder for fixing or adjusting the lower or upper jaw model with a baseplate, an adjustable levelling table mounted on it, a tilting arm which can be pivoted on the pillar of the base-plate for optional fixing of bite wall impression plates, model mounting plates or alignment keys for adjustment of the lower or upper jaw. The figure shows in this case a removable alignment key fixed to the pillars for adjustment of lower jaw and a bite wall stamp plate mounted on the pivoting tilting arm for determining the bite wall height for upper an lower jaw;

FIG. 3 shows a side view of the same apparatus with the tilting arm pivoted upwards and with the alignment key;

FIG. 3a shows a front view in part section of the levelling table arrangement;

FIG. 4 shows a front view of the same apparatus using the alignment key and the tilting arm pivoted downwards;

FIG. 7 shows a side view of the alignment key for the lower jaw for pillar adaptation;

FIG. 7a shows a front view of part of the alignment key as per FIG. 7 with a template inserted which can be turned to a limited extent;

FIG. 8 shows a side view of an alignment key fixed to an adapter for adjustment of the lower jaw in a construction for fixing to the pivoting tilting arm of the instrument holder;

FIG. 9 shows a plan view of the alignment key as per FIG. 8;

FIG. 10 shows a front view in part section of the adjustable levelling table arrangement on the base plate;

FIG. 11 shows a plan view of the apparatus with the levelling table attached and with the tilting arm upwards and an impression plate with centring plate fixed to the tilting arm;

FIG. 11a shows a plan view of the centric plate with a drawn gothic arch;

FIG. 12 shows a side view of the apparatus with the levelling table attached, the tilting arm downwards with an impression plate attached for bite wall height determination;

FIG. 13 shows a side view of an impression plate attached to an adapter in a different construction;

FIG. 14 shows a plan view of the impression plate as per FIG. 13;

FIG. 15 shows a side view in part section of the apparatus with the levelling table attached and the tilting arm downwards and the mounting plate fixed to it;

FIG. 18 shows a side view of an alignment bar held by means of an adapter, so that it can be detached, on the tilting arm, which can be displaced in the sagittal plane and can also be pivoted around a vertical axis, with a guiding edge for determination of the hard palate, and a forked stylus attached at the front to determine the covering fold in the labial frenulum area of the upper jaw model;

FIG. 19 shows a plan view of the alignment key as per FIG. 18;

FIG. 20 shows a side view of the instrument holder with a setting aid fixed to the tilting arm for lower jaw full prostheses in the usage position;

FIG. 21 shows a plan view of a dome-vaulted mount and two inserts as setting aids, with one insert fixed to the mount and the other removed;

FIG. 22 shows a front view of the mount with an insert as per FIG. 21;

FIG. 23 shows a front view of an insert;

FIG. 24 shows a side view of an insert;

FIG. 25 shows a side view of the mount with insert;

FIG. 26 shows a cross-section through the mount fixed to an adapter, holding two inserts at the same time;

FIG. 27 shows a side view of the mount with inserts as per FIG. 26;

FIG. 29 shows a side view of the instrument holder with a tooth template fixed to the setting aid;

FIG. 30 shows a cross-section through the mount of the setting aid with the tooth template inserted;

FIG. 31 shows a plan view of part of the mount with tooth template;

Figure 1:
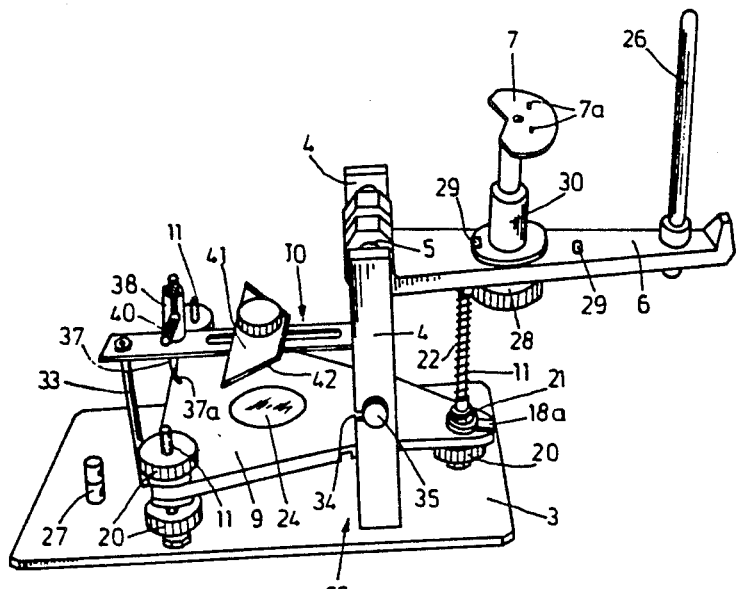

The module as per the invention for apparatus to prepare upper and lower jaw full prostheses has an instrument holder (66) as its basic equipment, on which the auxiliaries developed for the various work processes can be fixed in such a way that they can be detached, in the form of a levelling table (9), an alignment key (10/57) with adjusting stylus (37) and template (41/60), an impression plate (7/64), a mounting plate (8), an alignment bar (67), a setting aid (68) with dome (77,79) and/or tooth template (70).

The instrument holder has a flat baseplate (3) preferably square or rectangular in basic shape, supporting two parallel vertical pillars (4), which are fixed to this in the final third of the rectangular length of the baseplate (3). Between the two pillars (4) in the top end section, a tilting arm (6) is mounted such that it pivots around a horizontal axis.

On the baseplate (3) a levelling table is arranged which is infinitely adjustable in a vertical direction and can be inclined in infinitely variable directions to take a lower jaw model (1) or an upper jaw model (47), and a lower jaw model alignment key (10) for determining the symphysis and trigonal points is mounted in the space above the levelling table (9) beneath the tilting arm (6).

The levelling table (9) is preferably triangular in shape and grips with a triangular point between the two vertical pillars (4), so that then this triangular point is in the area behind the apparatus and a triangular transverse edge lies in front of the apparatus.

This levelling table (9) is held at all three corners by levelling spindles (11), which permit exact adjustment of every angle of inclination required, both sagittal and transversal, as well as the entire height of the levelling table (9). The levelling table (9) has a centreline formed from a milled groove (5, 6), which does not deviate from the sagittal axis of the apparatus even when adjusting to steep angles of inclination.

Likewise the transverse axis, which crosses the vertical axis (12) of the symphysis point (13), is not left during adjustment of the levelling table (9). This property is achieved by means of a vertical telescopic guide (14).

This telescopic guide (14) can be seen in FIGS. 4 and 10, having a bearing: (15) fixed to the baseplate (3) on the vertical axis (12) and a guide pin (16) in contact in it which can be displaced vertically, which is held by gimbal suspension in the levelling table (9) with a spherical end (17), so that on adjustment of inclination and height of the levelling table (9) there is movement in all directions, but the vertical axis (12) is maintained.

For this, the sphere (17) is arranged very close to the surface of the levelling table (9) (with only a very small distance between them), in order to maintain very low deviation from the centreline on adjustment of inclination of the levelling table (9).

Figure 5:
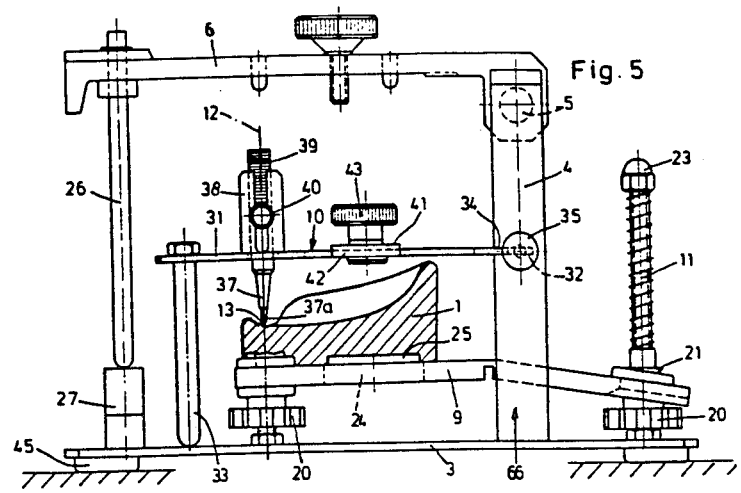
FIG. 5 shows a side view of the same apparatus using the alignment key and the lower jaw model arranged on the levelling table.
Figure 6:
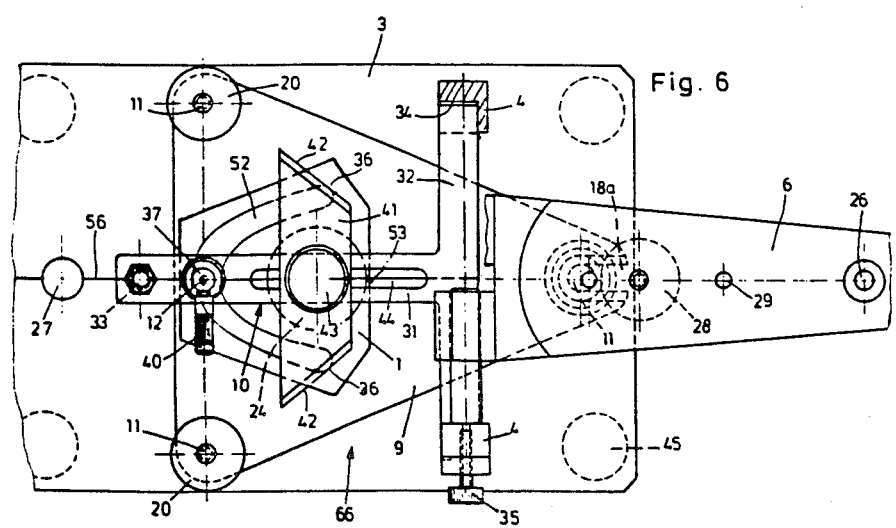
FIG. 6 shows a plan view of the same apparatus using the alignment key, the lower jaw model and the tilting arm pivoted upwards.
Figure 16:
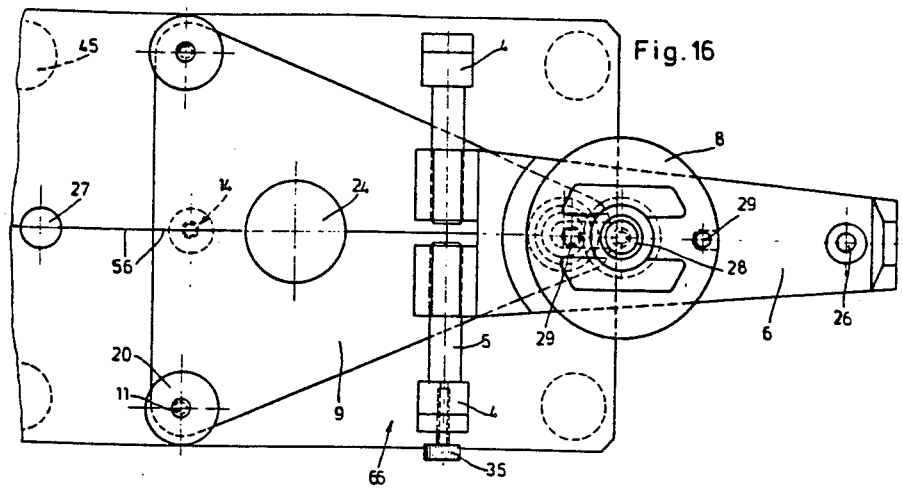
FIG. 16 shows a plan view of the apparatus with the tilting arm upwards with mounting plate and levelling table attached.

All three levelling spindles (11), Cf. FIGS. 5 and 10, are fixed Vertically to the baseplate (3) and formed of threaded bolts. The levelling table (9) has a hole (18) drilled in each corner of the triangle, which is larger in diameter than that of the levelling spindles (11) and grips with play with that of the levelling table (9) around the levelling spindles (11). Above and below each drilled hole (18), the levelling table (9) has a domed bearing (19), the vault of which continues in the depression of the drilled hole (18). Above and below the levelling table (9) there is a knurled nut (20) on each levelling spindle (11) for adjusting the levelling table (9), and each knurled nut grips in the bearing (19) with a domed catch (21), so that adjustment of the angle of inclination of the levelling table (9) is possible in relation to the vertical levelling spindles (11), nonetheless achieving secure fixing of the levelling table (9) in the set position. The levelling spindle (11) mounted in the triangular point of the levelling table (9) behind the pillars (4) is greater in height (length) than the two front levelling spindles (11) and on this levelling spindle there is only one knurled nut (20) acting against the underside of the levelling table (9) and on the upper side of the levelling table (9) a domed catch acts on the domed bearing (19), this catch being subject to the effects of a pressure spring (22) arranged around the levelling spindles (11), the counter bearing end of this being located on a cap nut (23) on the top end of the levelling spindle, this cap nut (23) at the same time forming a support bearing for the tilting arm (6) pivoted upwards and backwards, holding this then in a more or less horizontal position, as shown in FIG. 1. By means of the pressure spring (22) the triangular point of the levelling table (9) is always held down and height adjustment is effected with the lower knurled nut (20).

The triangular point of the levelling table (9) has a slot (18a) instead of the drilled hole (18), with which it grips around the levelling spindle.

As can be seen from FIG. 3a and FIGS. 1, 2 and 11, the slot (18a) has a swallowtail shape in cross-section and the domed bearing (21) grips in this slot (18a) with its dome, so that on adjustment of the levelling table (9), centring of the latter around the spring-loaded levelling spindle (11) is always guaranteed.

The invention also covers a construction in which the two front levelling spindles (11) have a pressure spring (22) but no upper knurled nuts (20), so that all three levelling spindles (11) are spring-loaded. The levelling table (9) has a permanent magnet (24), which is at the levelling table (9) position, on which the centre of the supporting surface of the lower jaw model (1) lies during adjustment. A ferrous disc (25) is set into the lower jaw model (1), so that the lower jaw model (1) can be fixed to the levelling table (9) by magnetic force. This type of fixing offers the possibility of manually displacing and adjusting the lower jaw models which ar to be adjusted, on the horizontal plane in any optional direction. The magnetic bond ensures that the lower jaw model (1) is prevented from unintentionally moving away from the set position, after each adjustment.

Figure 2:
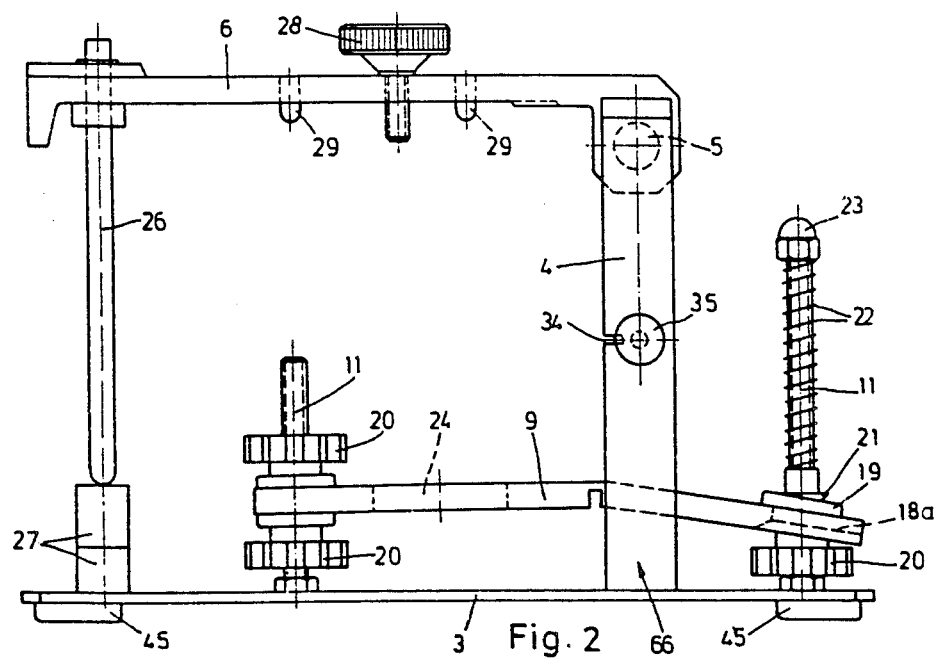
FIG. 2 shows a side view of the same apparatus with the tilting arm pivoted downwards and without the alignment key.

The tilting arm (6) is held so that it can pivot with one longitudinal end through the horizontal axis (5) on the pillars (4) and at the other longitudinal end has a reinforcing bolt (26) vertical to the arm length direction, which, when pivoted downwards, Cf. FIGS. 2 and 5, rests on the baseplate (3) or on a support bearing (27) fixed to the baseplate (3) and hence has a fixed set height when the apparatus is ready for use.

There is a knurled screw (28) in the tilting arm, with two fixing pins (29) in the space, which, together with the knurled screw (28), ensure fixing in the correct position of a mounting plate (8) under the tilting arm (6), Cf. FIG. 15, and also permit fixing in the correct position of an impression plate (7) by means of an adapter (30), Cf. FIG. 12, so that, again, by means of the adapter (30) the mounting plate (7) is maintained at a set height when the tilting arm (6) is pivoted downwards.

The alignment key (10), Cf. FIGS. 1, 3 to 7, has an adjusting rail (31) in a horizontal plane running in the longitudinal direction of the tilting arm (6), and this is fixed at one longitudinal end to the pillars (4), such that it is detachable, with a fixing strip (32) running transversally, and is supported at its other longitudinal end by means of a vertical reinforcing pin (33) fixed to the adjusting rail (31), on the baseplate (3), and fixed in the horizontal position by these mounts on both ends (32, 33).

The two pillars (4) have two slot-type insert guides (34) (insert slots) at about half-height level, one on the right and one on the left, in which the alignment key (10) is inserted with its fixing strip; in one pillar (4) at the insert slot point (34), a knurled screw (35) is screwed in, which acts on the front end of the fixing strip, thus fixing the alignment key (10) in the slot guide (34).

The reinforcing pin (33) can also be supported on a bearing support (33a) of the baseplate (3) (Cf. illustration with dot and dash line in FIG. 3), in which case the pin (33) is shorter and the alignment key (10) can thus be inserted more easily into the apparatus and extracted again (past the support bearing (27)).

The alignment key 10 has two adjustable parts, which are used to correctly determine the three salient alignment points of the lower jaw model 1, namely the symphysis point 13 and the centres of the two retromolar triangles, or more precisely the trigoni 36. The symphysis point 13 is always located on one of the vertical axes arranged in the correct position of one of the articulator geometries, and can be adjusted on this axis 12 in the range 10 to 25 mm below the masticaton plane. To this effect, an adjusting stylus 37 is provided on the adjusting rail 31 with an adjusting point 37a, such that this adjusting point 37a always lies on the vertical axis 12; the adjusting point 37a is formed as a straight or curved pin or constructed as a fork, with which the symphysis point 13 can be determined accurately, including the labial frenulum. The adjusting pin 37 is held vertically and can be adjusted in height in a guide sleeve 38. There is a millimetre scale 39 on the adjusting stylus 37 for identification of height adjustment. A fixing screw 40 fixes the adjusting stylus 37 opposite the guide sleeve 38, Cf. FIG. 5 and 7.

To determine the trigonal point 36, there is a trapezoidal template 41 on the adjusting rail 31 of adjusting key 10, and this is infinitely variable in displacement in a longitudinal direction on the adjusting rail 31, with the two lateral trapezoidal edges forming a measuring edge 42, which are at the height of the geometric mastication plane. The measuring edges 42 are ground as blades.

The template 41 can be displaced along the adjusting rail 31 and can be displaced and fixed infinitely variably over a limited length by means of a fixing screw 43, which grips through a longitudinal slot 44 of the adjusting rail 31. The trapezoidal taper of the bevelled measuring edges 42 of the template 41 is directed towards the pillars 4. The template 41 is inserted so that it can be displaced with a milled slot 41a on the adjusting rail 31. The slot 41a is hence constructed somewhat wider than the adjusting rail 31, so that the template 41 can be rotated +−5° in a horizontal plane and is hence adjustable (Cf. FIG. 7a).

The feet under the baseplate 3 are referenced 45.

The chronological sequence of all work processes possible with the alignment apparatus as per the invention is described below, excluding the condition of the work being carried out partly in dental practice and partly in the dental laboratory.

The main area of application is in the context of production of full upper or lower prostheses (28 type) or of individual upper or lower full prostheses.

The dentist first takes preliminary impressions of the upper and lower jaw. Gypsum models are then made from the impressions, bearing in mind that the plaster models (1 and/or 47) will have a magnetic disc (25) on the underside plane.

To ensure that the underside of the model is absolutely plane, it is recommended that the model be produced on a glass plate. A piece of polyethylene film is placed on the glass plate and then a magnetizable, preferably plane-ground galvanized disc of about 30 to 40 mm diameter. The plaster base of the lower jaw model 1 is placed on this and the cast impression put in position. After hardening of the plaster, the entire model is removed with the film which can easily be removed afterwards by a light pull. The model can be trimmed all round, but not the underside, for if a trimming disc is used several times or often, even if only lightly, it leaves a concave surface in each case. If the model underside is concave would not lie closely on the levelling table 9 of the apparatus and could be moved too easily from position by turning. The magnetic discs 25 in the models 1 should have a retention edge on the outside so that they cannot break away during use due to the force of the permanent magnets located in the levelling table 9 of the apparatus.

To hold the gypsum model with magnetic force on the levelling table, it is not essential to fit the model with a ferrous plate as described above. There are in the trade so-called split-cast systems which also use permanent magnet systems; these are therefore also suitable for use in conjunction with the module as per the invention.

Figure 17:
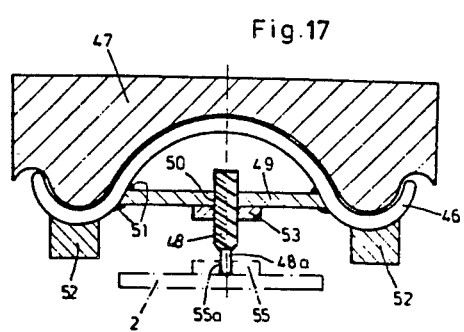
FIG. 17 shows a cross-section through an upper jaw model with denture plates and the reinforcing and adjusting screw mounted on them.

The denture plates 46 for both models are then to be prepared for both models (lower jaw model 1 and upper jaw model 47) with the maximum care. For this, the reinforcing and adjusting screw 48 in the upper jaw model 47 is to be used, which serves for centric determination by means of the "Gothic arch" (sagittal registration) and for effective individual bite depth adjustment (FIG. 17).

The denture plates 46 are preferably made from a self-polymerizing synthetic, which offers optimum true detail reproduction of impression contours, reducing to a minimum the risk of deformation both in the production process and in use of the denture plates 46 to a minimum. In shaping the lower jaw denture plate 46, it must be ensured that a sufficiently high wall is modelled on the jaw ridge, which serves to reinforce the denture plate 46 structurally, as well as giving a firm hold to the bite wall applied to it. The height of the reinforcing wall worked into the denture plate 46 must not, however, obstruct assembly of the centric plate 2 to be brought into contact with the bite wall.

In the upper jaw denture plate 46 (FIG. 17) the reinforcing and adjusting screw 48 for determination of centric and bite depth is to be applied as of manufacture. For this, a metal band 49, which has a threaded hole 50 to take the reinforcing and adjusting screw 48 in the centre of its surface, is to be incorporated horizontally in a transverse direction in the synthetic material, such that the threaded hole 50 is located some 15 mm away from the centre of the jaw ridge in a sagittal direction.

Fixing of the metal band 49 is by means of beads 51 of the same synthetic from which the denture plates 46 are made. A bite wall 52 of a silicone of particular hardness is then constructed (preferably with a Shore hardness value of A 90). The same procedure is followed for this as described for bite wall production for the lower jaw, but the adjusting key is to be used to adjust the model as per FIG. 18 or 19, and the bite wall impression plate as per FIG. 13 and 14 to establish the bite wall depth.

The hardened silicone walls, for both the upper jaw and lower jaw, can be cut back easily with a blade to the final width, but the height of the walls established with the bite wall die must not be touched in so doing. The upper surface of the walls should have a width of 5 to 6 mm and assume the same position in which the teeth rows will probably be in the finished prostheses. At the foot of the bite wall a groove should be cut in the direction of the jaw ridge, which runs around the wall lingually/palatinally as well as labially, and is used to take off excess casting material in later denture casting, to avoid excessive extension.

Finally, all edges made in cutting are to be polished with a rotary grinding stone, a miller, or a rotary emery paper strip.

The lower jaw model 1 is adjusted in the alignment apparatus. The completed denture plate 46 is then put to one side and is used again after adjustment.

On model 1, the three marking points are drawn in, at the front covering fold area, symphysis point 13 and the two retromolar triangles 36 in the back area, using a marking stylus. In addition, a mark 53 is applied indicating the centre axis of model 1 from a plan view, which is located on a line crossing symphysis point 13 in front and at the back the axis between the two trigonal points 36 in the centre. These markings are sufficient for adjusting the model 1 in the correct position.

The adjusting key 10 is prepared such that the trapezoidal template 41 is drawn forwards up to adjusting stylus 37 of symphysis point 13. Adjusting point 36a of adjusting stylus 37a is set to a mean value of 16 mm vertical height from the mastication plane to the symphysis point 13. The marked model 1 is now set on the levelling table 9, which has been lowered slightly beforehand with the levelling spindles, in order not to obstruct subsequent insertion due to model 1 projecting too far upwards. Adjusting key 10 is inserted into the guide slot 34 provided in pillars 4 until it stops and secured with the clamping screws 35 on the righthand pillar.

The actual levelling process then begins:

Model 1 is positioned manually on levelling table 9 in such a way that the marked symphysis point 13 reaches a point in a vertical direction beneath adjusting point 37a. In doing this, care must be taken with the position of the centre marking 53 on the rear edge of the model 1, which should be covered from vertical view from above with centreline 56 of the levelling table 9.

In order to maintain sufficient free space for levelling on the levelling spindles 11, the upper knurled nuts 20 of the two front levelling spindles 11 are rotated fully up. The two lower knurled nuts 20 are now rotated upwards simultaneously in order not to bring the model 1 out of the current balance, until the symphysis point 13 of model 1 is in contact with adjusting stylus 37, without removing the reinforcing pin 33 entirely forwards on adjusting key 10 from the baseplate 3.

The knurled nut 20 of the rear levelling spindle 11 is now adjusted wide enough upwards or downwards until the two trigoni 36 of the model 1 are at the height of the mastication plane. To ensure this, the trapezoidal template 41 is brought over the adjusting key 10 with its measuring edges 42 as near as possible to the marked centres of the trigoni 36 on model 1 and fixed with the corresponding adjusting screw 43. By looking parallel to the mastication plane, i.e. along underneath the trapezoidal template 41 it can be checked whether the markings 36 are at the right height, i.e. at the mastication plane level.

If it is found that markings 36 are at a different height, the model is balanced by adjusting the two front lower knurled nuts 20: to adjust the transverse inclination only, one of the two nuts 20 is lowered, depending on the required direction, and the other raised or reversed by a corresponding amount. By raising left nut 20, for example, and lowering the right nut, the left trigonum 36 is rised and the right trigonum 36 lowered, whilst the adjusted height of the symphysis point 13 is maintained. The height of the trigonal area is corrected as a whole with knurled nut 20 of the rear levelling spindle 11.

It is important to check the horizontal position of model 1 after the levelling process and correct it as necessary, as although each change in inclination maintains the corresponding points on levelling table 9 in their horizontal position, part of the markings on model 1 are above the level of levelling table 9, and hence stray slightly from their position with each change in inclination. Horizontal correction after each levelling process is hence unavoidable and must be carried out manually taking into account both the centre marking 53 in the rear part of model 1 and the symphysis point 13.

It is advisable to move the trapezoidal template 41 manually slightly away from the marking of the trigoni 36 during levelling or horizontal correction, to avoid obstruction from fixed parts of the apparatus.

When the levelling process is complete, the top two knurled nuts 20 of the front levelling spindles are turned downwards to fix the adjustment definitively. The adjusting key 10 can now be removed and model 1 is ready for assembly of the bite wall related to the mastication plane. If the front levelling spindles 11 are spring-loaded, the top knurled nuts 20 are not needed as counter nuts.

To create the bite wall, it is recommended that a very hard silicone be used (e.g. with a Shore hardness value of A 90 approx.). The silicone is mixed with the hardener in accordance with the proportioning instructions, to form a strand 1.5 to 2 cm thick and then applied to the denture plate following the contour of the jaw ridge identifiable on the denture plate 46. The wall 52 is now constructed approximately to the required form by hand, ensuring that the provisionaly hand-formed wall 52 projects 2 to 3 mm beyond the proposed final height.

The bite wall impression plate (template) 7 already inserted in the pivoted tilting arm 6 of the apparatus is tilted forwards and pressed with moderate pressure onto the silicone bite wall. The impression plate 7 limits the height of the silicone wall 52 to the height set at a mean value of 16 mm, measured from the symphysis point 13 to the mastication plane, while the reinforcing bolt 26 of the tilting arm 6 rests free of play on its bearing 27.

If a centric disc plate 2 has to be incorporated in the bite wall, this centric disc plate is to be slipped on with two holes onto two guide pins 7a located on the underside edge of the impression plate 7, secured with a small bead of adhesive wax to prevent it from detaching, and pressed together with the impression plate 7 onto the still soft silicone wall 52. This ensures that the centric disc plate 2 is in a horizontal position and at the probable height of the mastication plane.

After hardening of the silicone wall 52, the tilting arm 6 is folded back with impression plate 7. The bite wall 52, which also, where stated, has a groove for fixing the centric disc plate 2, is bonded to the denture plate 46 with a few drops of adhesive and can then be formed to the final shape. Both denture plates 46, upper and lower, are now prepared for denture casting and centric determination on the patient.

For adjustment and levelling, and for creating the bite wall of the upper jaw, exactly the same procedure is followed as for the lower jaw, but taking into account the condition that for the upper jaw the special adjustment key (FIG. 18 or 19) or bite wall impression plate (FIG. 13 or 14) is used.

Denture casting is undertaken separately for the upper and lower jaw. Denture casting is indispensable to ensure optimum positioning in subsequent centric and bite depth determination, and to achieve the most accurate result, must correspond with the contours of the future prosthesis. Checking of both denture plates 46 for perfect seating and freedom from pressure points before denture casting must not be omitted under any circumstances.

The centric and effective bite depth determination are then undertaken.

Once denture casting is complete for both jaws, the centric scribing plate 2 is bonded with a couple of beads of adhesive into the groove in the bite wall of the lower jaw denture plate 46 and the functionally-correct cast lower jaw denture plate 46 is set in the patient's mouth. The top jaw model 46 likewise fitted with the bite wall and formed correctly for proper functioning is placed in the patient's mouth and the patient is then asked to close his mouth. With the adjusting screw 48 in the upper jaw denture plate 46, which is fixed into the upper jaw denture plate 46 such that the point facing downwards formed as a writing and fixing stylus 48a approximately meets the centre of the scribing plate 2 fixed in the lower jaw denture plate 46 when the patient's mouth is closed, the individual bite depth of the patient is adjusted to the normal occlusion state. If the height of the silicone bite wall 52 is disturbed when doing this, the wall 52 of the upper jaw should be cut back with a blade until there is a space of 2 mm between the two walls, whilst the adjusting screw 48 of the upper jaw lies firmly on the centric scribing plate 2 when the bite depth is actually set. This records the bite depth. The dentist has various known methods available for determining bite depth.

To carry out centric determination, the two denture plates 46 are then removed from the patient's mouth and the adjusting screw 48 in the upper jaw denture plate 46 is secured against displacement, with a counter nut, for example (Cf. FIG. 17).

The centre of the scribing plate 2 is coated with a contrasting, fast-drying colour (e.g. dark nail varnish) and then both denture plates 46 are re-inserted. The patient then closes his mouth and makes exaggerated articulation movements, with forward and sideways movements in both directions.

As these movements are being made, the adjusting screw 48 of the upper jaw formed as a point 48a scratches a sagittal mark in the colour-marked surface of the centric scribing plate 2. This figure represents the so-called "gothic arch" 54 (Cf. FIG. 11a). The lines of this FIG. 54 exactly intersect the point which defines the centric point 54a of the prosthesis in the context of the articulation geometry.

The lower jaw denture plate 46 is then removed from the patient's mouth, and a disc with a hole 55a drilled centrally, of a diameter corresponding exactly to that of point 48a of the adjusting screw 48, is bonded to the centric scribing plate 2 such that the centre of the hole 55a lies exactly over the marked centric point 54 on scribing plate 2.

The side tooth area of the lower jaw denture plate 46 is then coated with mixed silicone on the left and right and re-inserted in the patient's mouth. The patient then closes his mouth, the grooved area in the silicone in the front tooth part permits visual inspection as the scribing stylus 48a catches in the hole 55a of the bonded plate 55 (FIG. 17) and the fresh silicone in the molar area completely fills out the space originally cut away between the bite walls.

After this, more fresh silicone is pressed into the front tooth area between the bite walls 52 and lightly smoothed over. After hardening of the "key", the dentist's task now consists in marking the lip closure line on the cleaned surface as well as drawing the intersection point of vertical axis 12 through symphysis point 13 on the lip closure line.

This completes the second casting and centric and bite depth determination.

When this process is complete, the upper and lower jaw impressions are keyed and arranged in the correct position with each other. This corresponds to the actual jaw conditions in the normal occlusion state. The arrangement shows a clear marking of the lip closure line, which is at the level of the actual mastication plane. To ensure that this arrangement is in the correct position of the articulator for production of the prosthesis, suitable functional models are made from the functional impressions.

The functional models are made on the basis of criteria as known and normal in dental practice. However, particular attention must be paid to plane construction with regard to lower jaw model 1 concerning its further use in the alignment and levelling apparatus for forming the underside of the model. In addition, the lower jaw model 1 must be formed such that it can easily be removed from the impression without damaging it. It must likewise be ensured that the silicone impression can be re-applied to model 1 without difficulty and without play.

The lower jaw model 1 now separated from the impressions, with a magnetic plate 25 in its underside, is then placed in the correct position corresponding to the articulator geometry, by adjustment with the apparatus, using the individual patient data taken from bite registration and centric determination. For this the same procedure is used as for the adjustment of the preliminary functional model. Beforehand, however, the adjusting stylus 37, which marks the symphysis point 13 in the adjusting key 10, is to be adjusted in height enough to measure from the symphysis point 13 to the marking on the lip closure line on the keyed bite template arrangement. Levelling and adjustment are then carried out as described previously.

The adjusting key 10 is now removed and the bite template arrangement with the upper jaw model, which has not yet been removed from the impression, is set on the adjusted lower jaw model. A mounting plate 8 to fit the articulator used is then applied and screwed to the tilting arm 6 of the apparatus. A quantity of plaster stirred to plastic state as required for use in the mounting plate 8 is then applied to the model arrangement and the tilting device tilted forwards with mounting plate 8 so that the mounting plate 8 immerses in the soft plaster. The reinforcing bolt 26 of tilting arm 6 must rest free from play on its bearing 27.

Once the plaster has set sufficiently and has reached a certain level of firmness, the transition between mounting plate 8 and upper jaw model 47 is cleaned and the arrangement is then left until the gypsum sets completely.

Then, by loosening the screw fixing 28, the mounting plate is detached from the tilting arm 6 and tilting arm 6 is tilted backwards.

The entire impression/model combination is removed from the levelling table 9 of the apparatus and inserted at the point provided on the upper part of the articulator to be used to complete the prosthesis.

After this, the articulator is set on end, so that the top of the articulator comes to rest over a support base, and the lower jaw model 1 is positioned with its underside uppermost. The lower part of the articulator is at this point pivoted backwards and supports a mounting plate for application of plaster on the lower jaw model. This process in principle follows the same procedure as described for application of plaster to the upper jaw model.

Both models are now in the absolutely correct position within the articulator geometry and in combination with the articulator, represent the prerequisite for correct functioning of prostheses made on these supports.

In addition to fixing the impression or mounting plate 7, 8, the screw fixing 28 with pins 29 also permits fixing of a wide range of adaptation devices for correct uptake of mounting plates on virtually all known articulator models, so that the apparatus as per the invention can be used in conjunction with all known articulator models.

FIG. 8 and 9 show a further construction of the alignment key (57) which has a mounting rail which can be fixed beneath an adapter (30) by means of a screw (58), this rail taking up the adjusting stylus (37) with adjusting points (37a), at one longitudinal end in the guide sleeve (38), and at the other longitudinal end area supporting a template, V-shaped in plan view, which is adjustable and can be displaced and pivoted around a vertical axis.

The V-shaped template (60) has a blade-type measuring edge (60a) on the outside edge of the two legs of the V. In the longitudinal direction of the mounting rail (59) lying on the centreline (56) there is a longitudinal slot, through which a screw (62) which grips the template (60) in the apex of the V, catches as a vertical pivoting axis; around the screw (61) there is a pressure spring (63) supported at one end on the mounting rail (59) and against a screw head (62a) at the other end, and this spring tightens and holds the template (60) clamping against the mounting rail (59) with compressive force.

The template (60) is infinitely variable in displacement in the area of the longitudinal slot (61) and can be pivoted infinitely variably around the screw (62) and hence can be adjusted exactly to the salient jaw points (13, 36), adjustment being maintained automatically by the spring (63).

This alignment key (57) is fixed to the tilting arm (6) by means of the adapter (30) in such a way that, in contrast to alignment key (10), it can be removed, and hence moved from top to bottom over the jaw model (1, 47) into its correct height position and held by the tilting arm.

The adjusting stylus (31) has the same components and functions as that on alignment key (10).

FIG. 13 and 14 show an impression plate (64), parabolic in shape, fixed to an adapter (30) by means of screws (58).

This impression plate (64) is used for lower jaw models (1) and to this effect has styli (7a) for the centric scribing plate (2); in the construction of the impression plate (64) for upper jaw models (47), the impression plate (64) is constructed without a stylus (7a) and has larger bevels (65) on the two corners.

In addition, the impression plate (64) can be constructed such that it can be used for both lower jaw models (1) and upper jaw models (47).

FIG. 18 and 19 show an alignment key (67) for aligning upper jaw models, in a reversed position in the instrument holder (66) on the levelling table (9) (with teeth uppermost).

This alignment key (67) is held onto the tilting arm (6) by means of an adapter (30) such that it can be removed and has a mounting rail (71) running longitudinally along the centreline (56) of the levelling table (9), this rail holding a transverse alignment strip (72) at its end facing the pillars (4) and an adjusting stylus (37) at the other longitudinal end.

The alignment strip (72) can be pivoted around a vertical pivoting axis formed by a screw (73) and held on the mounting rail (71) by means of this screw (73) in a longitudinal slot (74) with infinitely variable displacement.

Around the screw (73) is a pressure spring (73b) supported on the mounting rail (71) and screw head (73a), and this spring holds the alignment strip (72) against the mounting rail (71) by a clamping effect and fixes it automatically in any adjusted position.

The alignment strip (72) has an alignment edge that is continuous or divided into two sections on its longitudinal edge facing the pillars (4), and this edge is directed downwards and formed as a blade.

With this alignment edge (72a), the alignment strip (72) is adjusted to the hard palate (75) (FIG. 28) of the upper jaw model (47), so that this alignment strip (72) permits exact adjustment to variations in size and asymmetry of the upper jaw model (47) due to its capacity for pivoting and displacement.

Figure 32:
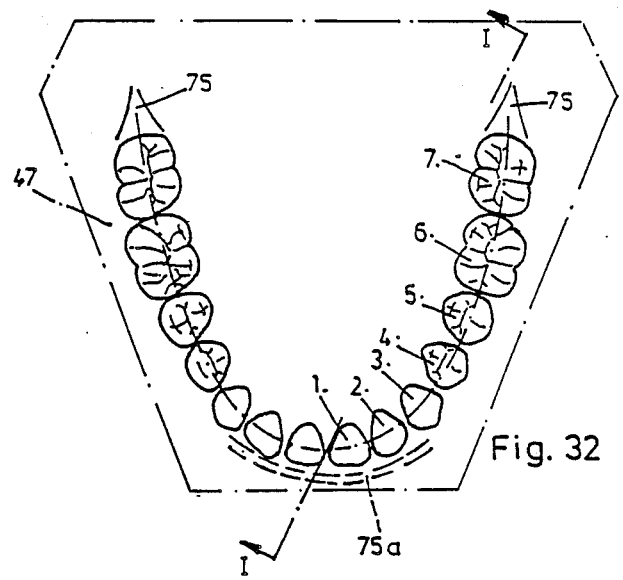
FIG. 32 shows an upwards view of the teeth of the upper jaw model with hard palate and covering fold.
Figure 32A:
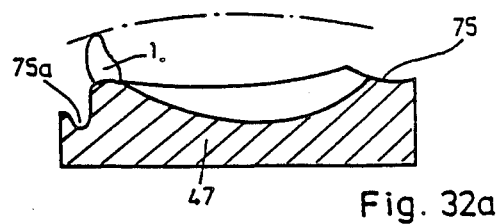
FIG. 32a shows a section through the upper jaw model as per intersection line I—I in FIG. 32.

The adjusting stylus (37) to determine the covering fold (75a) (FIG. 32 and 32a) is preferably held fixed (not adjustable in height) in the mounting rail (71). It can be available as a round stylus or as a fork.

An indicator stylus (76) is incorporated in the reinforcing bolt (26) which is housed in the reinforcing bolt (6) such that it can be removed. This indicator stylus (76) runs exactly horizontally in a sagittal direction and is at the exact height of the mastication plane level within the articulation geometry.

It is inserted in a hole (26a) drilled in the reinforcing bolt (26) and clamped in this such that it can be displaced. The end (76a) of the indicator stylus (76) which points in a sagittal direction is narrow and pointed and marks the incisal point between the two centre front teeth of the lower jaw prosthesis. At the other end, the indicator stylus (76) has a grip knob (76b).

The setting aid (68) as per FIGS. 20 to 28 for correct positioning of teeth 1 to 7 (8 defines the wisdom tooth) in lower jaw full prostheses is formed of a three-part dome (77, 79), which has a dome-vaulted mount (77) which can be fixed in position opposite a lower jaw model (1), with sagittal and transverse compensation curve (78) and two inserts (79) which can be pivoted and displaced as well as locked within the dome (dome vault/dome plane), for adjustment on the central fissure line (80).

The mount (77) consists of a frame domed in a vault shape in a longitudinal and transverse direction, which has two frame plates (77a) held together with a spacer mount (81) maintaining the space between them and at both longitudinal ends by a countersunk head screw (82) with knurled nut (83), and an insert slot extending over the entire frame width and over the entire frame length up to the spacer mount (81).

The spacer mount (81) is formed of a plate extending in the middle of the lengthwise area of the mount (77); a countersunk head screw (84) grips through the two frame plates (77a) from beneath and through the spacer mount (81) and with this countersunk head screw (84), the setting aid is fixed to an adapter (30) and fixed with the adapter (30) in the instrument holder (66), preferably an articulator as per FIG. 20.

The two countersunk head screws (82) likewise grip through the frame plates (77a) from beneath and all three countersunk head screws (82, 16) lie flush with the underside dome so that they do not obstruct.

Each of the two inserts (79) consists of a guide (79a) and a minimum of one, but preferably two, insert arms (79b) extending from one longitudinal end of the guide in a defined angle to a common guide side, so that the guide (79a) and the insert arms (79b) are formed of plate sections and are vaulted according to the dome in a sagittal and transverse direction. The insert arms (79b) can be fixed to the top of the guide (79a) by bonding, rivets, screws or suchlike, or integrated with the guide (79a). Each insert (79) grips with its insert arm (79b) in the insert slot (77b) of the mount (77) from one side, so that on adjustment to the central fissure line (80), one or both inserts (79) are inserted in the mount (77). If only one insert is used (79) after adjustment to the central fissure line (80) and setting of teeth 3 to 7, this insert (79) is removed and the second insert (79) then inserted and the same process followed on the opposite side.

The insert slot (77b) and insert arm (79b) are coordinated such that a clamping effect arises in the inserted position, which can be reinforced or supported by the screws (82), so that when knurled nuts (83) are used, overturning of the screw effect is prevented and the use of a tool excluded.

It is preferable for the guide (79a) to be made of a transparent synthetic and provide a straight line marking (80a) on the underside of the guide (79a) such as a coloured line, groove, raised section, etc., with which the guide (79a) can be aligned exactly on the central fissure line (80). The guide (79a) can also be just partially transparent, as shown in FIG. 21. In this case, the guide (79a) has a window, with a transparent part (79c) set into it, bearing the line marking (80a).

In addition, the guide (79a) can also consist of a non-transparent material, when the interior longitudinal edge of the guide forms the tooth guide edge aligned according to the central fissure line (80).

The insert (79) introduced with its insert arm (79b) into the insert slot (77b) can be displaced infinitely variably in a lateral direction "A" and a longitudinal direction "B", and can be pivoted infinitely variably in the arrow direction "C" (FIG. 21), permitting individual adjustment of the insert (79). In each adjusted position, the insert (79) is always within the dome plane, i.e. the insert (79) is only moved within the dome vault.

The mount (77) and two inserts (79) can be made of metal, such as light alloy, with a non-transparent or transparent area for the markings (80a), or of transparent synthetic.

The guide (79a) and the insert arm which may be attached or integrated with the guide (70a) are preferably rectangular in basic shape, but may also be of other suitable basic shapes.

FIGS. 20, 22 and 25 show the mount (77) accommodating just one insert (79) and the height of the spacer mount thus corresponds to the thickness of the insert arm (79b), which also dictates the slot height. With this construction, an insert (79) is first introduced and aligned on the central fissure line (80); after setting teeth 3 to 7, the insert (79) is removed and the second insert (79) can then be inserted and used for the opposite row of teeth 3 to 7.

FIGS. 26 and 27 show a construction for simultaneous use of both inserts (79). In this case, the spacer mount (81) is constructed with a height of twice the thickness of the insert arm (79b) as a plate section or two superimposed plate sections, so that the slot (77b) permits insertion of both inserts, which then rest on top of each other with their insert arms (79b).

It is preferable if the spacer mount (81) is made of two plate sections of the same thickness, corresponding to the thickness of the insert arms, so that if required the mount (77) can be used in turn for single-sided or double-sided insertion of the insert (79), by using one or both spacer mount plate sections.

On the baseplate (17) of the instrument holder (66) (articulator), the lower jaw model (1) is held on a mounting plate (85), aligned to the symphysis point (13) and the trigoni (36).

The reinforcing bolt (26) is positioned in the tilting arm (6) and can be adjusted in height, supported on an adjusting table (88) of the baseplate (3), this table being pivoted around a horizontal axis (88a), the longitudinal axis of the reinforcing bolt (26) remaining aligned with the pivoting axis (88a).

The mastication plane (87) of the dome (77, 79) is fixed by the adapter (30) which forms an integral fixed unit and is defined in height in relation to the articulator used, so that when the tilting arm (6) is folded down the correct mastication plane (87) is always obtained with the adapter (30) and dome (77,79), The depth of the mastication plane (87) can also be adjusted by means of an adapter (30) which can in itself be adjusted in height. In this case, the adapter (30) is constructed so that it can be displaced telescopically, and is fixed at the set height by means of a fixing screw (89) (FIG. 20).

Around the vertical reinforcing bolt (26) there is an indicator stylus (76) with a point (76a), which is positioned such that it can be adjusted in height and fixed. The reinforcing bolt (26) has a mark at the height of the imaginary mastication plane (87), and the indicator stylus (76) is adjusted to this and its point (76a) then lies on the imaginary mastication plane (87) and hence on the incisal point.

For adjustment of the adapter (30) to the mastication plane (87), the tilting arm (6) is pivoted downwards and the mount (77) falls on the point (76a) and is hence at the right height position; the adapter (30) can now be fixed with the fixing screw (89) and the dome (77, 79) is located exactly at the bite depth.

The longitudinal axis (69) of the mount (77) runs along the longitudinal axis (56) of the instrument holder (66), so that even after removing the adjusting stylus (76), the centre axis of the jaw remains identifiable, using the centreline (6) on the mount (77) for orientation.

Figure 28:
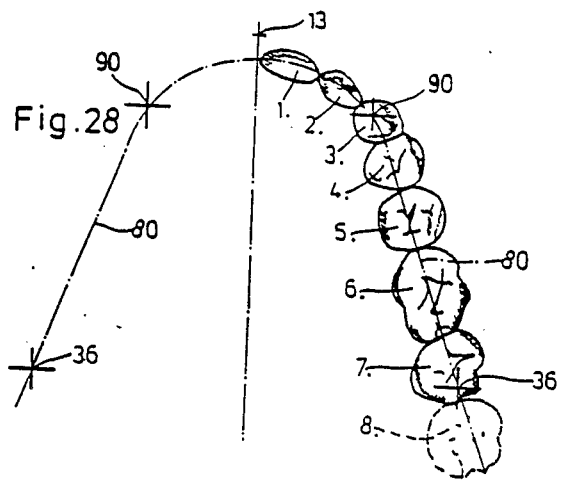
FIG. 28 shows a schematic front view of the two central fissure lines of the lower jaw with a row of teeth arranged on the half lower jaw.

FIG. 28 shows a schematic plan view of a lower jaw with a row of teeth comprising teeth 1 to 8. The central fissure lines (80) run between the canine tooth points (90) and the trigoni (36).

The functional procedure for setting the teeth for the lower jaw full prosthesis using the setting aid (68) in conjunction with the articulator is as follows:

1. The lower jaw model (1) is inserted in the articulator using the mounting plate (85) aligned at the main points, i.e. the symphysis point (13), trigoni (36) and mastication plane (87).
2. The tilting arm (56) with the setting aid (68) mounted on it by means of the adapter (30) is pivoted downwards in the usage position shown in FIG. 20, so that the setting aid (68) is held at the correct height by the reinforcing bolt (26) and the rigid adapter (30) or by the adjusting stylus (76) and height-adjustable, fixable adapter (30), and the height of teeth 3 to 7 to be set is finally defined in relation to the mastication plane (87).
3. The trigonal points (36) are to be marked on the model (1). The line (80a) is then fixed to their distal point. The canine tooth point (90) is cetermined from the position of the canine after the front row of teeth (1 to 3 left and 1 to 3 right) has been set to suit the anatomical conditions. The centre of the trigonal point on the lower jaw model and the centre point of the cusp of the canine are to cover the marking line (80a) of the dome side, on displacement and pivoting of the insert (79) or both inserts (79).
4. Locking of the adjusted insert or inserts (79) is achieved by clamping the insert arm (79b) in the insert slot (77b) automatically or with the knurled nuts (83).
5. Teeth 4 to 7 can now be set.
6. First a row of teeth 4 to 7 is set using an insert (79) and then the insert (79) is changed for the second insert (79), and the same process is followed for the opposite side. If both inserts (79) are used on the mount (77), both rows of teeth can be set in the same process.

Teeth 1 to 7 are located in the sagittal and also the transverse compensation curve (78), the dome (77, 79) having the same curve, intersecting the imaginary mastication plane at the height of the 3rd tooth, and the 6th and 7th in the transition area.

In order for the line (80a) to meet the underside of the transparent inserts (79)—guide (79a), the effect of optical refraction is avoided, hence permitting optimum accuracy of adjustment from above.

Setting of the lower jaw teeth 3 to 7 is carried out in accordance with the set central fissure line (80) and thus fulfills important basic prerequisites for functionality of the prosthesis to be made.

If two inserts (79) are inserted in the mount (77) at the same time, a spacer mount (79a) is provided as per FIG. 26 with one insert (79) between the guide (79a) and the insert arm (79b), so that the insert arms (79b) of both inserts are superimposed and the two guides (79a) extend in the same dome vault (78).

To ensure that the right or left lower first tooth is set in the correct position, a tooth template (70) formed of a dummy tooth (91) with insert arm (92), as in FIG. 29, and this is held with its insert arm (92) so that it can be detached and with the medial edge (91a) of the dummy tooth (91) on a centreline (93) provided on the mount (77) of the setting aid and can be aligned along this centre line (93) in a sagittal direction.

This tooth template (70) permits setting of the first right or left tooth in the correct position, when a coating or wax (1b) is applied to the jaw ridge (1a), making a flat covering following the form of the jaw ridge (1a) within the limits obtained by the impression, so that the jaw ridge (1a) is covered by this wax layer (1b) and is not visible.

The mesial edge (91a) of the dummy tooth then forms an application surface for the right or left 1st tooth. The mesial edge (91a) lies vertical. The centreline (93) forming the prosthesis symmetry axis is marked by a milled groove in the lower frame plate (77a), which extends in a longitudinal direction and thus in the sagittal direction of the mount (77)

The insert arm (92) is at an angle, preferably a right angle to the mesial edge (91a) and is formed as a flat pad which grips between the two frame plates (77a) of the mount (77) and is locked by the screw (82) with knurled nut (83) in the mount (77) in its set position.

This insert arm (92) forms a striking edge (92a) which acts in conjunction with one longitudinal edge (77c) of the mount (77), in particular of the lower frame plate (77a); this striking edge (92a, 77c) ensures that the insert depth of the tooth template (70) is limited transverse to the longitudinal direction of the mount and at the same time ensures that the mesial edge (91a) thus always lies on the centreline (93). Depending on the various prostheses, the tooth template (70) can then be displaced infinitely variably in a sagittal direction (in the longitudinal direction of the mount (77)), so that the mesial edge (91a) always remains on the centreline (93).

The dummy tooth (91) with the insert arm (92) is preferably formed as one part out of synthetic or metal; it may also be non-tooth shaped, i.e. as a pad, cam, or suchlike.

This tooth template (70) is used for the right and left insert and to this effect has an insert arm (92) pointing to the left or right, depending on whether it is a left or right insert, so that two tooth templates (70) are available for setting the first teeth.

For adjustment, the tooth template (70) is first positioned with its insert arm (92) between the frame plates (77a) of the mount (77) and then moved on the centreline (93) into the correct position to suit the anatomical conditions of the jaw.

The tooth template (70) is then locked with the nurled nuts (83). The mount (77) with the tooth template (70) is then pivoted upwards with the tilting arm (6).

The wax coating (template) (1b) is now applied to the jaw ridge (1a), forming the wax base for setting the full lower prosthesis, and the tilting arm (6) is then pivoted downwards again, so that the dummy tooth (91) presses into the wax coating (1b). For this it is advisable to soften the point where the tooth penetrates the wax coating, using a hot wax blade. The right or left row of teeth 1 to 3, and then the left or right row, can now be set in the wax coating (1b).

The tilting arm (6) is then pivoted upwards again and the tooth template (70) removed from the mount (77) and the guide inserts (79) then inserted in the mount (77) and aligned to the central fissure line, so that the other teeth 4 to 7 can then be set.

The reason and purpose of the tooth template (70) is firstly to ensure accurate setting of teeth 1 to 3 and secondly to facilitate alignment of the inserts (79) on the central fissure line, as the marking lines of the inserts (79) are covered by the central fissure line, which in turn intersects the cutting cusp of canine tooth 3 in a mesial direction as well as the centre of the trigonum retromolar in a distal direction.

The front edge of the dummy tooth (91) corresponds in shape to the lateral profile of the front surface of a lower front tooth 1 and is arranged in the average correct axis inclination of a correctly positioned front tooth 1.

I claim:

1. Apparatus for preparing upper and lower jaw full prostheses, the apparatus comprising: p1 (a) an instrument holder comprising a baseplate, two upright pillars mounted on the baseplate and a support arm mounted between the two pillars for pivotal movement about a generally horizontal axis;
   (b) a support platform for a jaw model supported on the baseplate of the instrument holder and including means by which the height and inclination of the support platform with respect to the baseplate can be adjusted;
   (c) a lower jaw alignment member for determining the symphysis and trigoni points of the jaw model detachably supported by the pillars in a position above the said support platform, a stylus carried by the alignment member, means for adjusting the height of the stylus with respect to the symphysis point of the jaw model, a template for determining the trigoni of the jaw model carried by the alignment member, and means for adjusting the horizontal position of the template with respect to the alignment member to determine the trigoni;
   (d) a second lower jaw alignment member selectively mounted by means of an adapter onto the support arm of the instrument holder, means for adjusting the height of the second alignment member with respect to the symphysis point of the jaw model, a template supported by the second alignment member, and means for adjusting the horizontal position of the template with respect to the second alignment member to determine the trigoni;
   (e) an impression plate selectively mounted by means of an adapter onto the support arm of the instrument holder for lower and/or upper jaw models;
   (f) a mounting plate selectively mounted by means of an adapter onto the support arm of the instrument holder for lower and/or upper jaw models;
   (g) an upper jaw model alignment plate selectively mounted by means of an adapter onto the support arm of the instrument holder, a stylus carried by the upper jaw model alignment plate, means carried by the upper jaw model which includes a guide edge whose position can be adjusted to the hard palate of the upper jaw model;
   (h) a setting aid for enabling correct positioning of teeth in lower jaw full prostheses selectively mounted by means of an adapter onto the support arm of the instrument holder, the setting aid including a dome-shaped mount including means by which it can be fixed in a position opposite to a lower jaw model with sagittal and transverse compensation curve, and two pivotably mounted inserts lockable within the dome of the mount for adjustment of the central fissure line; and (i) a tooth template selectively carried by the setting aid and comprising a dummy tooth formed with an insert arm whose position can be adjusted and locked in a position opposite to a lower jaw model with the mesial edge of the dummy tooth aligned in a sagittal direction on a centreline of the mount.

2. Apparatus as claimed in claim 1 wherein the support platform is of triangular configuration and is positioned on the baseplate such that the rearmost one of its three corner sections passes between the two upright pillars with the respective corner sited in the final third of the baseplate, the support platform being formed in each corner with an aperture through which extends an externally threaded spindle secured to the baseplate and the diameter of each aperture being greater than that of the respective spindle to facilitate limited movement of each spindle within its respective aperture, the two apertures each being formed with upper and lower bearing surfaces into each of which a domed-shaped extension of an adjustment nut threaded onto the respective spindle protrudes, the third rearmost aperture being formed with a lower bearing surface into which a dome-shaped extension of an adjustment nut threaded onto the respective spindle protrudes, this said spindle being of greater length than either of the other two spindles and having positioned about its shaft a spring which urges an insert carried by the spindle shaft into the upper open end of the respective aperture, the spindle of greater length including a cap nut screwed onto its upper end to provide a bearing surface for the support arm when it lies in one of its two pivoted positions.

3. Apparatus as claimed in claim 2 wherein the rearmost aperture takes the form of an open-ended slot into which the longer of the three spindles protrudes, the rearmost corner of the support platform being supported between the spring-urged insert and the dome-shaped extension of the respective adjustment nut.

4. Apparatus as claimed in claim 2 wherein a telescopic guide is mounted on the baseplate at a location between the two forward spindles which coincides with the vertical axis of the symphysis point, the telescopic guide including a guide sleeve secured to the baseplate within which a vertically movable guide pin formed with a spherical end is located, the arrangement being such that the spherical end of the guide pin is positioned a short distance below the upper surface of the support platform.

5. Apparatus as claimed in claim 3 wherein the support arm carries a vertical post, the free end of which rests on the baseplate to support the support arm in a horizontal position when the support arm is in the other of its two positions, the support arm carrying a knurled screw and two fixing pins on its underside for selectively attaching the mounting plate or the impression plate thereto by means of an adapter.

6. Apparatus as claimed in claim 1 wherein the alignment member is supported at one end within guide slots formed in the two pillars and at its other end by means of a post whose free end rests on the baseplate to support the alignment member in a horizontal position above the support platform, a clamping screw being provided to lock the said one end of the alignment member with respect to the pillars.

7. Apparatus as claimed in claim 6 wherein the alignment member comprises a first elongate member which extends between and is supported at its ends within the guide slots of the two pillars and a second elongate member which lies normal to the first member and which carries the post for supporting the alignment member.

8. Apparatus as claimed in claim 7 wherein the stylus carried by the alignment member is supported for vertical displacement within an upright guide sleeve secured to the said second elongate member of the alignment member, the position of the stylus within the guide sleeve being locked by means of a locking screw.

9. Apparatus as claimed in claim 1 wherein the template carried by the alignment member is of trapezoidal configuration, two side edges of the template defining measuring edges of the trigoni, the template being supported on said second elongate member of the alignment member and being movable longitudinally of the said second member within a slot formed in said second member and lockable in any required position by means of a locking screw, the respective dimensions of the template and the slot being such that the template can rotate within the slot in a horizontal plane about angles lying in the range of + −5 degrees.

10. Apparatus as claimed in claim 1 wherein the said second lower jaw alignment member includes a detachable mounting rail which extends generally longitudinally of the support platform and the baseplate, and wherein the template is of "V" shaped configuration whose outer edges define measurement edges, the arrangement being such that the template can be displaced relative to the mounting rail in a longitudinal and an angular sense, and that the template can be locked in any required position.

11. Apparatus as claimed in claim 1 wherein the upper jaw alignment plate includes an elongate mounting rail formed with an elongate slot into which a spring loaded spindle is located to hold in position a guide strip which includes a downwardly extending guide edge, the position of the guide strip being adjustable both lengthwise of the elongate slot and angularly with respect to the mounting rail.

12. Apparatus as claimed in claim 11 wherein the stylus carried by the upper jaw alignment plate is mounted on the mounting rail at its end remote from the guide strip.

13. Apparatus as claimed in claim 1 wherein the impression plate is parabolic in configuration and includes a bite template including means for attaching to the template a centric scribing plate.

14. Apparatus as claimed in claim 1 wherein the domeshaped mount comprises two superimposed frame plate each of which is formed with a central spacer to define between the superimposed plates a slot to receive the removable inserts, the height of the central spacers corresponding in height with the thickness of the insert arm and that of each of the pivotably mounted inserts for selective or simultaneous insertion of the insert arm and the pivotably mounted inserts.

15. Apparatus as claimed in claim 14 wherein the two frame plates of the dome-shaped mount are joined together by means of screws which pass through apertures formed in the opposite ends of the frame plates, the heads of the screws being flush with the underside of the mount and the mount itself being secured to its adapter by means of a countersunk screw whose head lies flush with the underside of the mount.

16. Apparatus as claimed in claim 14 wherein each pivotably mounted insert comprises a guide which can be aligned to the central fissure line, and two arms pivotably connected to the guide for clamping within the insert slot, the guide of each insert being formed at least partially of transparent material, on the underside of which is provided with first and second marking means.

17. Apparatus as claimed in claim 1 wherein the mesial edge of the dummy tooth forms an application surface for the right or left first tooth and the tooth template has a right or left insert arm for inserting of the dummy tooth.

18. Apparatus as claimed in claim 14 wherein the centreline of the mount comprises a groove set in the lower of the two frame plates, the edge of the insert arm of the dummy tooth co-operating with the adjoining edge of the mount to limit the extent of insert arm insertion such that the mesial edge of the dummy tooth is aligned in a sagittal direction on the centreline of the mount.

19. Apparatus as claimed in claim 18 wherein the insert arm lies in a plane normal to the mesial edge of the dummy tooth is formed integrally with the dummy tooth.

* * * * *